United States Patent [19]

Leif

[11] 4,351,611
[45] Sep. 28, 1982

[54] MONITORING OF A DETECTION ZONE UTILIZING ZERO ORDER RADIATION FROM A CONCAVE REFLECTING GRATING

[75] Inventor: Robert C. Leif, Coral Gables, Fla.
[73] Assignee: Coulter Electronics, Inc., Hialeah, Fla.
[21] Appl. No.: 189,505
[22] Filed: Sep. 22, 1980
[51] Int. Cl.³ .............................................. G01J 3/18
[52] U.S. Cl. ................................ 356/328; 250/461.2; 356/318
[58] Field of Search ................ 356/39, 305, 317, 318, 356/328, 334; 250/461 B

[56] References Cited
U.S. PATENT DOCUMENTS
3,493,303  2/1970  Exton ................................. 356/305

OTHER PUBLICATIONS

Leif et al., Clinical Chemistry, vol. 23, No. 8, Aug. 1977, pp. 1492-1498.

Primary Examiner—F. L. Evans
Attorney, Agent, or Firm—Gerald R. Hibnick

[57] ABSTRACT

Disclosed is an optical flow system wherein individual particles, which are sequentially suspended in a fluid flow, are irradiated at a detection zone with an excitation source to generate radiation signals, which in turn are dispersed by a concave reflection grating for subsequent detection and measurement. The radiation signals which are not dispersed from the grating but are reflected from the grating, are further reflected by a conjugate mirror to form a projected image of the detection zone suitable for viewing with a screen or eyepiece.

3 Claims, 1 Drawing Figure

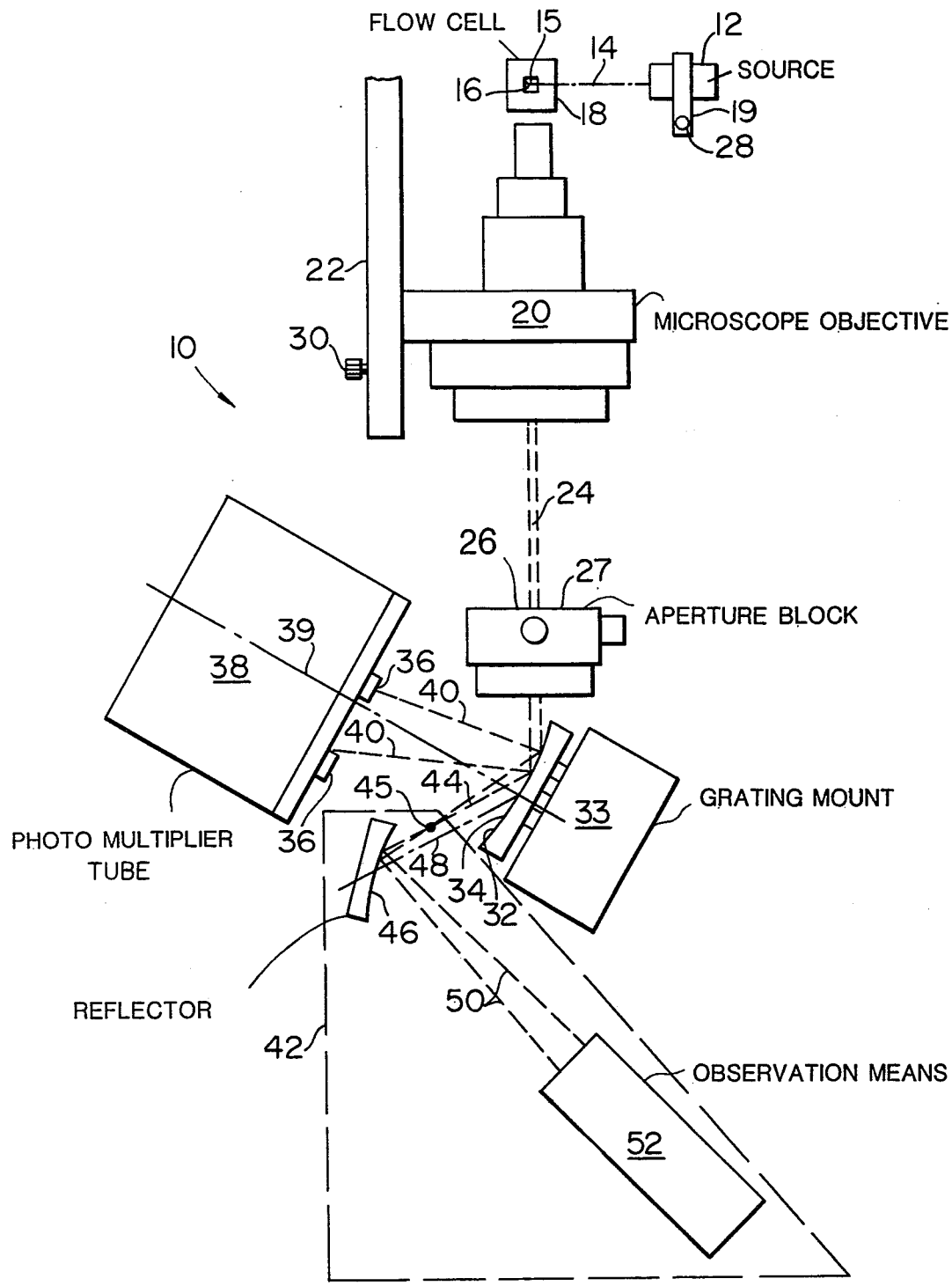

MONITORING OF A DETECTION ZONE UTILIZING ZERO ORDER RADIATION FROM A CONCAVE REFLECTING GRATING

FIELD OF THE INVENTION

The present invention relates to optical flow systems wherein gratings are used to disperse radiation signals into line spectrums for subsequent analysis.

DESCRIPTION OF THE PRIOR ART

Automated optical flow systems are widely used for observing individual particles as they flow in suspension sequentially through a small detection volume, in which they are irradiated with an excitation beam. The irradiation of the particles produces measurable radiation signals, such as light absorption, fluorescence and light scatter. These radiation signals provide particle descriptors or parameters which are used to count, identify and analyze the particles. The radiation signals are translated by electro-optic means to analog electrical quantities.

Cytology research has revealed that complex problems, such as leukocyte differential counting, require multiple descriptors such as the use of specific stains for eosinophils, monocytes, basophils, and T and B lymphocytes, as well as the determination of DNA content of each cell, thereby resulting in the use of up to six separate fluorochromes. To separate the various fluorescent radiation signals of differing wavelengths, a holographic grating, capable of focusing a dispersed spectrum onto a photomultiplier tube or like means has been employed. These various features and considerations and the present state of the art are set forth in "Development of Instrumentation and Fluorochromes for Automated Multiparameter Analysis of Cells", R. C. Leif et al., CLINICAL CHEMISTRY, Vol. 23, No. 8, 1977, pp. 1492-1498.

The inherent problem in the above described prior art flow system becomes evident when the operator of the instrument attempts to align and focus the light collecting optics. The standard procedure requires a mirror to be interposed across the radiation signal to provide an alternative optical path for focusing the entire beam through an eyepiece. Consequently, there is presently no way to monitor radiation signal reception, or focus and align the optical system, without interrupting the signal reception.

The applicant, while developing the hereinafter described invention, was employed and supported by the Papanicolaou Cancer Research Institute of Miami, FL.

SUMMARY OF THE INVENTION

The invention is directed toward monitoring means for observing a detection zone of an optical flow system wherein individual particles, which are sequentially suspended in a fluid flow, are irradiated at the detection zone with an excitation source to generate radiation signals, the radiation signals in turn being dispersed by a grating for subsequent detection and measurement. The monitoring means intercepts and utilizes heretofore unused, relatively organized radiation, which has been reflected from the grating and not dispersed therefrom, to form a projected image of the detection zone for subsequent observation either with an eyepiece, or on a screen or like observation means.

In operation, the monitoring means makes it possible to directly observe the detection zone, thereby allowing the user to focus and align the optical part of the flow system, without interrupting signal reception. This permits the user to readily optimize optical focusing of the optical elements in order to obtain maximum efficiency from the grating. Moreover, the monitoring means can be employed to observe the detection zone while the flow system is in operation; therefore permitting the user to gather data, while the user is able to determine at all times whether the optical system is functioning.

BRIEF DESCRIPTION OF THE DRAWINGS

Further objects and advantages of the present invention will become apparent as the following description proceeds, taken in conjunction with the accompanying drawings in which:

The sole FIGURE shows a schematic diagram of the flow system in accordance with the invention.

DESCRIPTION OF THE PREFERRED EMBODIMENT

The drawing shows an optical flow system which is generally indicated by reference character 10. A radiation source 12 provides a light beam 14, which irradiates individual particles suspended in a liquid stream passing through a detection zone 15, the detection zone 15 being disposed inside of a square orifice 16 of a cube shaped flow cell 18. The radiation source 12 is slidably secured on an adjustable mount 19. Radiation signals, produced by the excitation due to the beam 14, are collected by conventional collection optics in the form of a microscope objective arrangement 20, which is mounted on an adjustable objective mount 22. Typically, the radiation signals will be a composite of stimulated fluorescent radiation and scattered laser radiation, although the radiation signals can include other types of radiation. The radiation signals proceed from the microscope objective arrangement 20 in the collimated beam 24, through a filter aperture 26. The filtering aperture 26 is capable of filtering out stray radiation by limiting the image to that of the liquid stream and is formed in a block 27. The above described optical system for particle illumination and radiation collection is illustrative of one of several possible optical arrangements that can be used with a monitoring arrangement of the invention, to be described hereinafter. For example, some of the prior art arrangements for particle illumination and resultant light collection therefrom are illustrated in U.S. Pat. No. 3,710,933 to Fulwyler et al. and U.S. Pat. No. 3,989,381 to Fulwyler. No matter what the optical arrangement, it is necessary for the operator of the instrument to focus and align the optical part of the system. Depending upon the specific optical arrangement, a laser beam, a flow cell and/or the light collecting lenses and mirrors can be adjustably moved for the purposes of alignment and focusing. For instance, in the illustrative optics of the preferred embodiment, the operator manually rotates one or more alignment control knobs 28 to align in up to three dimensions the beam 14 to properly intersect the detection zone 15. Likewise, the operator manually manipulates one or more focus knobs 30 to adjust in up to three dimensions the spacial relationship between the detection zone 15 and the collection lens of the microscope objective arrangement 20 to focus the radiation emanating from the detecting zone 15. Generally, the other prior art arrangements have one or more collection lenses or mirrors that must be aligned and positioned to collect radiation signals.

The collimated radiation signals, after passing through the aperture 26, impinge upon a grating 32, employed to disperse the radiation into spectrum lines. The grating 32 is secured on a mount 33. In the preferred embodiment, the grating 32 is of the reflection type, and more specifically, is a commercially available, concave holographic grating, wherein a system of interference fringes are formed on a photosensitive layer of a concave surface 34 of the grating 32. It will be apparent to those skilled in the art that other types of known reflection gratings or transmission gratings can be employed. Generally, these other gratings are made by mechanical ruling, with a diamond point, so as to provide a large number of equidistant, parallel grooves on a glass or metal surface. Consequently, dispersed radiation is created by interference fringes with holographic gratings, ruled grooves with reflection gratings and slits or grooves with transmission gratings. In the drawing, the grating 32 disperses the radiation signals in a line spectrum at adjustable entrance slits 36 of a photomultiplier tube 38, as shown by light rays 40. The photomultiplier tube 38 and the grating 32 are positioned along a radiation dispersion axis 39. The employment of the grating 32 in the flow system 10 is representative of the construction of a prior art arrangement.

A unique monitoring means 42 is used with the heretofore described optical flow system 10. With most commercially available gratings, such as the grating 32, approximately 50 percent of the radiation that strikes the grating is reflected, rather than being dispersed into the line spectrum. The reflected radiation signals are shown in the drawing by light rays 44. Since the collimated beam 24 impinges upon the concave surface 34, the reflected light rays 44 illustrate relatively organized radiation converging to a focus 45. An image forming means, preferably in the form of a concave conjugate mirror 46, is cooperatively positioned on a radiation reflection axis 48 to correct at least partially for the divergence of the radiation signals illustrated by the rays 44, such divergence being caused by the focusing action of the grating 32. In the illustrated embodiment, the conjugate mirror 46 has a substantially spherical configuration. However, depending upon the configuration of the grating 32, the configuration of the conjugate mirror 46 can vary substantially. The conjugate mirror 46 is constructed to substantially undo the focusing effect of the grating 32 in its zero order. For example, if the grating 32 focuses light in only one direction so as to create a line focus, then the conjugate mirror 46 could have cylindrical configuration. However, in the illustrated embodiment, the light is focused in two directions; thereby resulting the preferred spherical configuration. If the conjugate mirror 46 is positioned to intercept the radiation signals prior to their arrival at the focus 45, then a convex conjugate mirror 46 would be required. However, due to the short focal length of the focus 45 in the illustrated embodiment, this is not the preferred implementation. In either case, the conjugate mirror 46 would have a circular cross-sectional configuration. It will be obvious to those skilled in the art, that other types of reflectors can be used. For example, instead of a concave spherical mirror 46, a concave reflecting paraboloidal mirror, having a parabolical cross-sectional configuration, can be used and instead of a convex spherical mirror, a convex reflecting ellipsoidal mirror, having an elliptical cross-sectional configuration, can be used. All of the possible reflectors, to be used for image forming, have conic cross-sectional configurations. The use of reflectors, as compared to refractors, is preferred since refractors have chromatic aberration problems. However, a lens could be used in place of the conjugate mirror 46. The angle the radiation reflection axis 48 forms with the radiation dispersion axis 39 is dependent upon the relative angle of the incoming collimated beam 24. As illustrated by light rays 50, the radiation signals reflect from the conjugate mirror 46 in a relatively collimated or slightly divergent beam with the focusing, caused by the concave grating 32, being substantially corrected. The image forming means can be modified to provide any beam configuration desired. Moreover, if a planar grating is used in place of a concave grating 32, the image forming means can be eliminated. With at least one commercially available, holographic grating, there is some focusing of the reflected light in two perpendicular, spaced-apart line focuses. In such a case, a spherical mirror or cylindrical mirror for undoing the first line focus has been found to be sufficient. The radiation signals from the concave grating 32 are projected to an observation means 52 which can take the form of a conventional microscope eyepiece arrangement, a projection screen or like observation means. In summary, it will also be apparent to those skilled in the art that other types of gratings will reflect radiation in different ways, so that different optical elements other than the conjugate mirror 46, or in some cases no optical elements, will be needed to appropriately correct for radiation modification caused by the grating.

Additionally, conventional fiber optics can be used in place of the conjugate mirror 46. In such a case, one end of the fiber bundle would preferably be positioned at the focus 45 with, for example, a magnifying lens at the other end of the fiber bundle.

In operation, the operator of the flow system 10 will observe the projected image of the detection zone 15 on the screen or through the eyepiece, without interrupting signal reception by the photomultiplier tube 38. Hence, the user can observe the focusing of the collection lens of the microscope objective arrangement 20 and can continue to monitor the focusing during operation. If the projected image proves to be undesirably disorganized, then further focusing can be undertaken or the operation of the flow system 10 can be terminated.

Heretofore, the flow system 10 has been described as being used for the study of particles, such as biological cells. Another implementation of the flow system 10 is in the art of chromatography, wherein optical flow cells commonly are used to analyze a fluid chromatographic effluent. The term "particle" is defined herein to include the fluorescing or absorbing molecules of the fluid chromatographic effluent.

Although particular embodiments of the invention have been shown and described here, there is no intention thereby to limit the invention to the details of such embodiments. On the contrary, the intention is to cover all modifications, alternatives, embodiments, usages and equivalents of the subject invention as fall within the spirit and scope of the invention, specification and the appended claims.

What is claimed is:

1. An optical flow system, wherein means are provided for measuring radiation signals generated when particles, which are suspended in a fluid flow, are irradiated in a detection zone, said flow system having a concave reflecting grating disposed to intercept the radiation signals and disperse the radiation signals into a spectrum, said concave reflecting grating substantially having a line focus for "zero order" reflected radiation, the improvement of the flow system comprising:

monitoring means, disposed to receive the reflected radiation from the grating, for observing the detection zone;

said monitoring means including a reflector, the line focus of the grating being disposed between the grating and said reflector, said reflector having a concave surface oriented to receive the reflected radiation from the grating;

said monitoring means includes observation means, disposed to receive the reflected radiation from said reflector, for observing an image of the detection zone.

2. The optical flow system according to claim 1 wherein said observation means includes a screen.

3. The optical flow system according to claim 1 wherein said observation means includes an eyepiece.